United States Patent [19]

Simmons

[11] 3,938,500

[45] Feb. 17, 1976

[54] AUTOMATED NEWBORN HEARING SCREENING APPARATUS AND METHOD

[75] Inventor: F. Blair Simmons, Portola Valley, Calif.

[73] Assignee: The Board of Trustees of Leland Stanford Junior University, Stanford, Calif.

[22] Filed: Aug. 19, 1974

[21] Appl. No.: 498,450

[52] U.S. Cl. ................... 128/2 Z; 128/2 S; 179/1 N
[51] Int. Cl.² ............................................ A61B 5/12
[58] Field of Search..... 128/2 N, 2 S, 2.1 B, 2.05 R, 128/2 Z; 179/1 N

[56] References Cited
UNITED STATES PATENTS

| | | | |
|---|---|---|---|
| 2,768,236 | 10/1956 | Allison................. | 179/1 N |
| 3,105,876 | 10/1963 | Mullin et al. ......... | 179/1 N |
| 3,392,241 | 7/1968 | Weiss et al............ | 179/1 N |
| 3,395,697 | 8/1968 | Mendelson............ | 128/2 Z |
| 3,439,358 | 4/1969 | Salmons............... | 128/2 S X |
| 3,658,052 | 4/1972 | Alter.................... | 128/2 S |
| 3,799,146 | 3/1974 | John et al............. | 128/2 Z X |

*Primary Examiner*—Kyle L. Howell
*Attorney, Agent, or Firm*—Flehr, Hohbach, Test, Albritton & Herbert

[57] ABSTRACT

A hearing screening apparatus of the type for measuring hearing of a human subject by measuring the change in subject motor activity in response to an unexpected auditory stimulus. The apparatus includes an audio signal reproducer spaced from the subject and a motion transducer coupled to receive subject motor activity and having an output. Means is provided for recording the transducer output as a function of time. Control means is provided for recording subject base line motor activity and at a predetermined time simultaneously transmitting an auditory test signal stimulus via said reproducer and recording subject motor activity response to said test signal stimulus.

9 Claims, 2 Drawing Figures

U.S. Patent   Feb 17, 1976   3,938,500
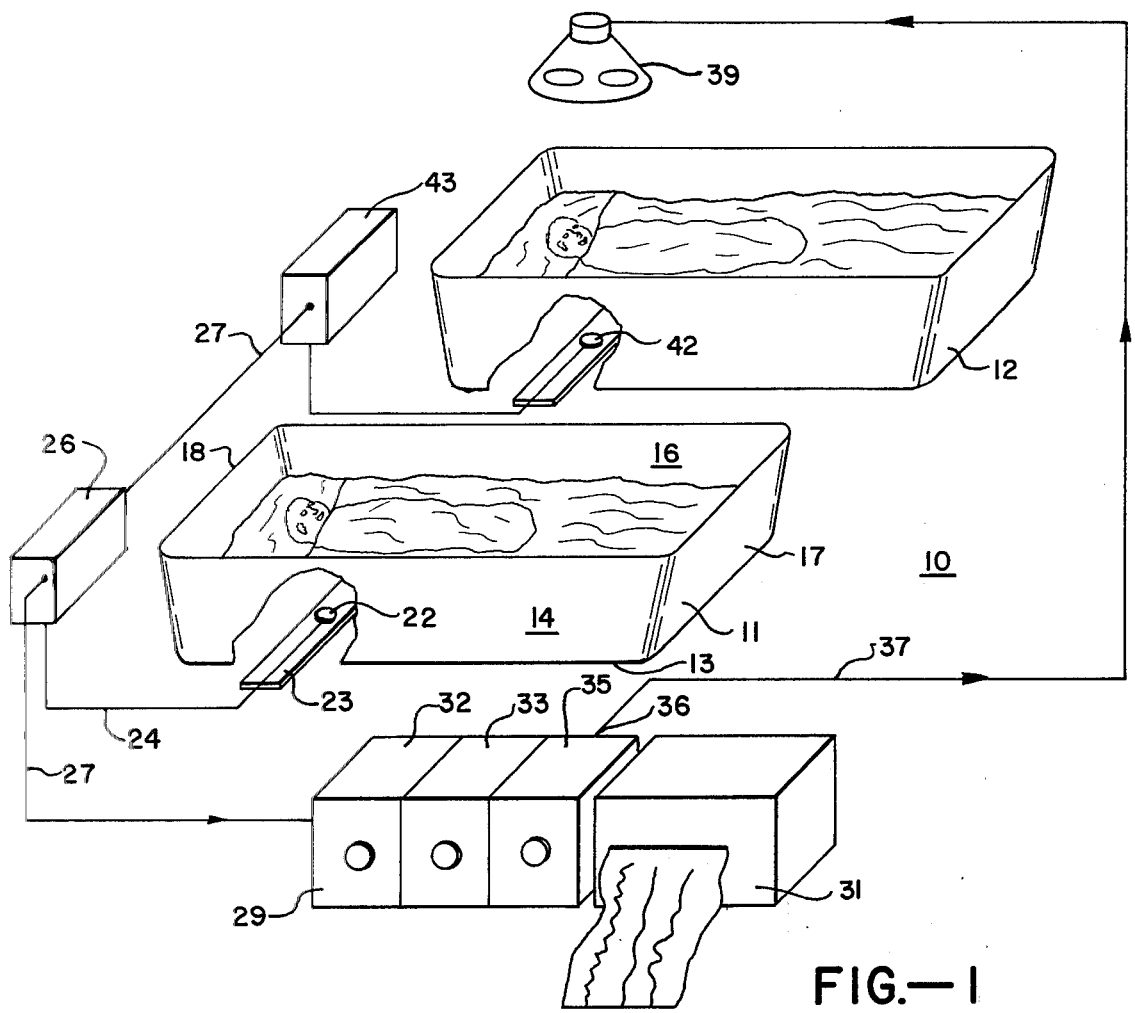
FIG.—1
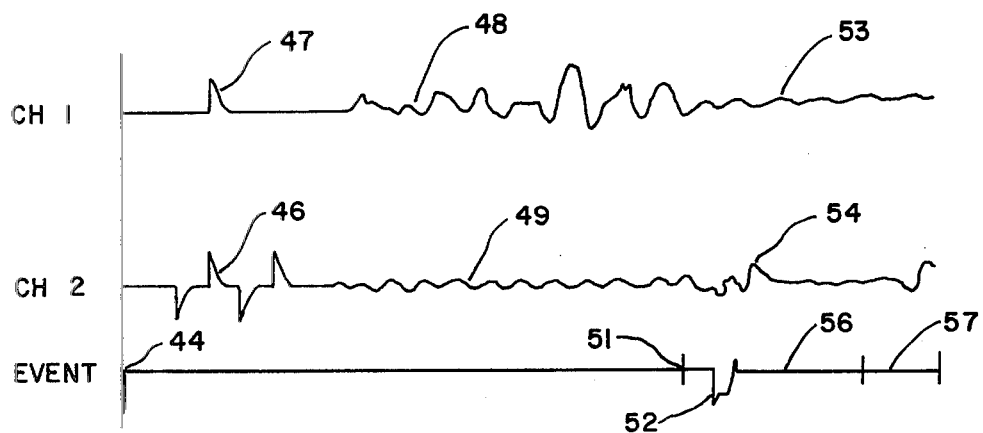
FIG.—2

AUTOMATED NEWBORN HEARING SCREENING APPARATUS AND METHOD

BACKGROUND OF THE INVENTION

This invention relates generally to an apparatus for hearing screening and a method for measuring the hearing response of a human subject. More particularly, this invention relates to an apparatus and method for utilizing said apparatus for measuring hearing of a human subject by measuring the change in subject motor activity in response to an unexpected auditory stimulus.

Although hearing screening of the human subject in the first few months of life is known in the art, such screening is on a subject-by-subject individual basis, requires highly trained personnel, the cost is excessive and the screening yields only subjective test results. Thus there is a need for an apparatus and method for hearing screening at substantially low cost without the necessity of highly trained personnel.

OBJECTS AND SUMMARY OF THE INVENTION

Accordingly, it is a general object of the present invention to provide an apparatus and method for hearing screening at greatly reduced cost, without requiring highly trained personnel and to yield objective test results.

It is a particular object of the present invention to provide an apparatus for hearing screening of human subjects with minimum intrusion in their environment and wherein the apparatus is automated to operate at predetermined levels and times within the environment.

It is a further particular object of the present invention to provide a method for measuring hearing of a human subject by subjecting the subject in its normal environment to predetermined testing levels at unexpected time periods for measuring the change in subject motor activity in response to the unexpected auditory stimulus.

The foregoing and other objects of the invention are achieved in a hearing screening apparatus, and method for utilizing said apparatus for measuring hearing of a human subject by measuring the change in subject motor activity in response to an unexpected auditory stimulus. The apparatus includes an audio signal reproducer spaced from the subject and a motion transducer coupled to receive subject motor activity and having an output. Means is provided for recording the transducer output as a function of time. Control means is provided for recording subject base line motor activity, and at a predetermined time simultaneously transmitting an auditory test signal stimulus via said reproducer and recording subject motor activity response to said test signal stimulus.

DESCRIPTION OF THE DRAWINGS

FIG. 1 is an isometric view, partly in cross-section, showing a portion of a hospital nursery environment, including plural standard nursery cribs and the hearing screening apparatus integrated with minimum intrusion into the nursery environment.

FIG. 2 is a representative output of the invention including plural measurement channels.

DESCRIPTION OF THE PREFERRED EMBODIMENT

Referring to FIG. 1, the hearing screening apparatus is shown integrated to minimize intrusion in a nursery environment 10 including at least one standard nursery crib 11. Additional crib 12 may also be provided. Crib 11 may be a standard nursery crib having a conventional base or support. Crib 11 has a bottom wall 13 and spaced upstanding and generally confronting side walls 14 and 16. Crib 11 further includes end walls 17 and 18 positioned to cooperate with walls 14 and 16 to enclose and form a box-shaped crib having an upwardly facing opening 19. Crib 11 is of suitable size to include comfort padding material such as a matress and bed clothing, on the inner walls thereof and further contain the human subject, such as a newborn baby and thereby present the subject with the normal nursery environment.

A motion transducer 22 is coupled to receive subject motor activity and may be positioned under the matress, or on any of the walls of said crib. The transducer may be positionally located and mounted to particularly emphasize the monitoring of specific motor activity. The positional location partially determines the waveform frequency response of the detected subject motor activity by virtue of the coupling via the mass and elasticity of the crib structural components. It has been found that a motion transducer such as model No. 8101M15 Pixie Transducer (Endevco, Co., Pasadena, Calif.), may be first embedded in silicon rubber and then fastened to a steel strap, approximately one-eighth inch in thickness. The strap 23 having the transducer 22 affixed thereto is coupled to receive subject motor activity. It has been found that coupling the strap and transducer to bottom wall 13 generally underlying the subject central body portion emphasizes the response to the subject's respiratory movement. Transducer 22 has lead means 24 connected thereto to couple said transducer to external electrical circuitry. Lead means 24 may couple the transducer output to crib identifier 26 and via a common signal BUS 27 to remote control means 29 and indicating means 31. Crib identifier 26 may be conventional digital pulse generation circuitry providing a unique series of pulses from each identifier and the associated crib during operation of the apparatus. Crib identifier 26 may be omitted in the case of a single crib apparatus and lead means 24 coupled directly to remote control means 29.

Control means 29 includes amplification and filtering means for amplifying and emphasizing the desired frequency range. Preferably a logrithmic amplifier may be used having suitable gain to amplify the output of transducer 22. A low frequency bandpass filter is connected to the output of amplifier 32 to emphasize the low frequency range output of transducer 22. The output of the band pass filter 33 is coupled to the input of recording means 31 such as a multiple channel strip chart recorder. Control means 29 further includes timing means 35 for actuating the apparatus at predetermined times as will be later seen.

Control means 29 includes a transmit signal output 36 and a transmit signal BUS 37 which is connected to an audio signal reproducer 39. Audio signal reproducer 39 may be a loudspeaker placed to overly the opening 19 of crib 11 and may be mounted in the nursery ceiling above said crib. Alternatively when only a single crib is to be used, such as for screening of higher-rise subjects in an ICU (Intensive Care Unit) nursery the transducer 22 may be positioned over the crib opening 19 and spaced from the subject.

Turning to operation of the apparatus, and the performance of a screening measurement, plural cribs 11 and 12 may be positioned to underly reproducer 39, with respective transducers 22 and 42 coupled via identifiers 26 and 43 to channels 1 and 2 of control means 29. Operation of the apparatus may be seen from the strip chart 31 output showing the timing diagram and sequence of the apparatus, FIG. 2. Upon initiation of a screening sequence, event output trace 44 is present as are the respective channels 1 and 2 outputs. Crib identifiers 26 and 43 at the initiation of a sequence are responsive to a pulse train generated by control means 29. For example, a sequence of seven pulses may be generated by control means 29 and sent simultaneously via BUS 27 to all crib identifiers. The first of the seven pulses may be utilized to reset the logic in each of the respective crib identifiers 26 and 43. Each of the next 5 pulses, that is pulses 2–6, may be selectively transmitted or coupled through identifiers 26 and 43 depending on the interconnection of circuitry included therein. Each identifier may include a 5-bit serial diode detector array capable of being connected to pass a unique combination of pulses. Identifier 26 may be connected to transmit or couple only the first of the 5 pulses, identifier 43 the first and second of the 5 pulses, and so on with the identifier associated with a seventh crib (not shown) transmitting pulses 2–4 thus corresponding to a binary 111 signal. The respective pulse trains of each of the crib identifiers are transmitted via lines 24 and 27 to the appropriate channels of recorder 31. The seventh pulse generated by control means 29 serves to turn off the crib identifiers and switch the outputs of the respective transducers 22 and 42 back on the signal lines 24 and 27.

After the identification sequence, the subject baseline motor activity trace is recorded, trace 48 representing an active subject and corresponding motor activity at channel 1 and trace 49 showing sleeping subject and a corresponding motor acvity at the output of channel 2. The baseline motor activity may be monitored, preferably for a period of approximately 10 seconds. Near the end of the subject's baseline activity a personnel warning tone such as a 40 db, SPL (sound pressure level) 4KH$_z$ tone may be transmitted via reproducer 39 to prevent startling personnel that may be present in the nursery. Although the apparatus is adjusted to provide a uniform 92 db SPL level at the cribs, the intensity is of course greater for personnel who may be standing immediately under reproducer 39.

At event time 52, the 92 db SPL signal is initiated while simultaneously continuing to record the subject motor activity. The test signal stimulus may be administered for a period of approximately 1 second. Trace portions 53 and 54, respectively, show the response by the subject to the unexpected signal stimulus. It has been found that a strong motor activity response within a four second time period 56 after the test signal is initiated indicates a "strong" response. A response within an additional two second period 57 indicates a "weak" response. The test cycle is then completed with respect to cribs 11 and 12 and the cycle may be later repeated and selectively administered at predetermined times dependent on the adjustment of timing means 35. For example twenty tests may be administered during a 24 hour period and may be administered in groups of four, spaced, for example, 8 minutes apart at times of 12 noon, 11 p.m., 3 a.m. and 6 a.m. Thus it is clear that the subject will have his hearing tested thirty or more times during the hospital stay. Further it has been found that by spreading the test schedule over multi-hour periods, mainly at night when the nursery routine is least active and when most subjects will be in their cribs, a large enough sample per subject is obtained to statistically insure that each subject's behavioral response state will be optimal at least part of the time. Moreover, the apparatus may operate 24 hours each day, and 7 days each week a period which would be excessively difficult and expensive to monitor with human observers.

The response recordings for given periods may be collected and scored. Further, untrained personnel can learn to score very quickly because little judgement is required on the part of the scorer. The scorer need only determine whether there is a change in motor activity which coincides with the test sound. It has been found that a subject may be considered to hear and thus pass the hearing screening test if his response rate is better than 20% or if two definite startle or arousal responses are present within a two second period after the test sound is initiated at event 52. Of course, "silent" tests may be interjected without the knowledge of the scorer to insure proper scoring. Moreover, subsequent follow-up with the parents and/or the physician or record, in addition to the compilation of statistical results will increase the long term predictability of the apparatus and the testing method.

It has been found that the type of sound does influence response rates. A cribside sound level of between 92 and 93 db SPL was initially selected because it yielded an average response rate greater than 30% and was within the range of stimuli used in prior art screening. It is believed that the approximate 90 db level is probably low enough to insure that most subjects with a hearing loss of more than 60–65 db will fail to respond. It has been found that the most effective sound stimuli is a 2–4 kH$_z$ band of noise. A tone which was swept rapidly upwards from 2–4 kH$_z$ for a period of about 50 miliseconds was also utilized. However it has been found that by comparison on the same population of subjects the noise band stimuli produced 44% and sweep tone 28% positive responses.

Thus it is apparent that there has been provided an apparatus and method for hearing screening at greatly reduced cost, without requiring highly trained personnel and yielding objective results. In particular an apparatus has been provided for hearing screening of human subjects with minimum intrusion in their environment wherein the apparatus operates at predetermined levels and times within the environment.

I claim:

1. In a hearing screening apparatus of the type for measuring hearing of a human subject by measuring the change in subject motor activity in response to an unexpected auditory stimulus, the apparatus comprising, an audio signal reproducer disposed to stimulate the subject with audio energy, means for supporting said human subject, a motion transducer coupled to said support means serving to provide an electrical output signal responsive to movement of the support means responsive to movement of the human subject, means for recording the transducer output as a function of time, control means for recording a signal for the subject's baseline motor activity and at a predetermined time simultaneously transmitting an auditory test signal stimulus via said reproducer and recording a signal for the subject's motor activity response to said test signal stimulus.

2. An apparatus as in claim 1 wherein said signal reproducer includes means providing a 2–4 kH$_z$ noise stimulus which ranges from 90 to 95 db sound pressure level.

3. An apparatus as in claim 1 wherein the baseline recording time is approximately 10 seconds, the audio signal one second in duration, and said means for recording includes means providing a recorded response which includes a strong response period of 4 seconds from initiation of said test signal and a poor response period extending for an additional two second period.

4. An apparatus as in claim 1 further comprising wherein a signal plural measurement channels including plural transducers coupled to plural support means and plural recording means, said apparatus simultaneously recording baseline activity, transmitting test signals and recording responses as a function of time for each channel together with identification means for each channel operative preceding said baseline recording.

5. In a hearing screening apparatus for newborn babies of the type for measuring hearing of a baby by measuring the change in the motor activity of the baby in response to an unexpected auditory test signal, the apparatus comprising, a crib, an audio signal reproducer disposed to direct an audio signal to said crib, a motion transducer coupled to the crib to detect movement of said crib, said transducer having an electrical signal output, means for recording the transducer electrical signal output as a function of time, control means for recording the baseline motor activity of a baby disposed in the crib and at a predetermined time simultaneously transmitting an audio test signal via said reproducer and recording the motor activity response of the baby to the test signal.

6. An apparatus as in claim 5 wherein said signal reproducer includes means providing a 2–4 kH$_z$ noise stimulus which ranges from 90 to 95 db sound pressure level.

7. An apparatus as in claim 5 wherein the baseline recording time is approximately 10 seconds, the audio signal 1 second in duration, and said means for recording includes means providing a recorded response which includes a strong response period of 4 seconds from initiation of said test signal and a poor response period extending for an additional 2 second period.

8. An apparatus as in claim 5 further comprising plural measurement channels including plural transducers coupled to plural cribs and plural recording means, said apparatus simultaneously recording baseline activity, transmitting test signals and recording responses as a function of time for each channel together with identification means for each channel operative preceding said baseline recording.

9. In a method for hearing screening of a baby in a normal nursery baby crib environment utilizing a test signal reproducer, a motion transducer coupled to said crib for receiving the motor activity of the baby, control and recording means coupled to said transducer the method comprising, recording the baseline motor activity of the baby, and simultaneously transmitting an auditory test signal of a predetermined level via said reproducer and detecting and recording the motor activity of the baby to said test signal.

* * * * *